United States Patent [19]

Marko et al.

[11] 4,402,796

[45] Sep. 6, 1983

[54] SEPARATION OF CHLOROSILANES BY LIQUID EXTRACTION

[75] Inventors: Ollie W. Marko; Stefan F. Rentsch, both of Carrollton, Ky.

[73] Assignee: Dow Corning Corporation, Midland, Mich.

[21] Appl. No.: 419,855

[22] Filed: Sep. 20, 1982

[51] Int. Cl.³ .............................................. C07F 7/20
[52] U.S. Cl. .................................... 203/43; 556/466; 556/472
[58] Field of Search ................................... 203/43–46, 203/58, 57, 68, 69, 70, 52; 556/466, 472, 465

[56] References Cited

U.S. PATENT DOCUMENTS

| | | | |
|---|---|---|---|
| 2,388,575 | 11/1945 | Sauer et al. | 556/466 X |
| 2,738,359 | 3/1956 | Hyde | 556/466 |
| 3,007,956 | 11/1961 | Linville et al. | 556/466 |
| 3,352,765 | 11/1967 | Warner | 203/70 |
| 4,012,289 | 3/1977 | Haskell | 203/58 |

*Primary Examiner*—Wilbur L. Bascomb, Jr.

*Attorney, Agent, or Firm*—Richard A. Kaba

[57] ABSTRACT

This invention relates to a method of separating close-boiling chlorosilanes from mixtures by employing the technique of liquid extraction with sulfolane and a hydrocarbon compound as co-solvents. The hydrocarbon compound employed is substantially immiscible in sulfolane and is present in sufficient amounts so that two liquid phases are formed, one being suloflane-rich and the other being hydrocarbon-rich. The mixture of chlorosilanes is intimately mixed with the two solvents and allowed to partition between the two phases. The preferred liquid extraction procedure is where the sulfolane and hydrocarbon solvent are in a countercurrent relationship within an extraction tower. Experimentally determined selectivity coefficients show that mixtures of (1) dimethyldichlorosilane and methyltrichlorosilane, (2) phenylmethyldichlorosilane and phenyltrichlorosilane, and (3) trimethylchlorosilane and tetrachlorosilane can be successfully separated by the techniques of this invention.

8 Claims, No Drawings

SEPARATION OF CHLOROSILANES BY LIQUID EXTRACTION

BACKGROUND OF THE INVENTION

During the reaction of methyl chloride with silicon a complex mixture of chlorosilanes is produced. This complex mixture is normally separated by fractional distillation. Two of the largest volume chlorosilanes, dimethyldichlorosilane and methyltrichlorosilane, have boiling points sufficiently close that distillation columns of 200 or more plates are often required to obtain pure components. Therefore, the separation of dimethyldichlorosilane and methyltrichlorosilane on a commercial scale is expensive in view of both capital and operational costs.

The separation of other close-boiling chlorosilanes also represent a difficult and challenging problem to the silicone industry. For example, tetrachlorosilane and trimethylchlorosilane form an azeotropic mixture which, naturally, cannot be separated by simple fractional distillation. The separation of methylphenyldichlorosilane and phenyltrichlorosilane is complicated by their high boiling points (>200° C.) as well as the closeness of their boiling points.

One object of the present invention is to provide an alternative method for the separation of close-boiling chlorosilanes which avoids problems associated with the conventional separation techniques currently employed by the silicone industry. Another object of the present invention is to provide a method in which close-boiling chlorosilanes can be separated by using the technique of liquid-liquid extraction. Another object is to provide a method by which close-boiling chlorosilanes, which cannot be separated by conventional fractional distillation, can be separated. Other objects of the present invention will be apparent to those skilled in the art upon consideration of the specification.

In addition to the conventional fractional distillation techniques, other methods have been proposed for the separation of close-boiling chlorosilanes. For example, U.S. Pat. No. 3,007,956 teaches that the separation of close-boiling chlorosilanes can be facilitated by the use of certain dinitrile compounds using extraction techniques. The separation of the azeotropic mixture of tetrachlorosilane and trimethylchlorosilane was not reported in U.S. Pat. No. 3,007,956. The technique of U.S. Pat. No. 3,007,956 has not been employed widely, if at all, in the silicone industry perhaps because of the toxic nature of nitrile compounds in general. The separation of the azeotropic mixture of tetrachlorosilane and trimethylchlorosilane has been carried out by a variety of methods including, for example, the addition of acetonitrile or acrylonitrile. According to U.S. Pat. No. 2,388,575, the nitriles form an azeotrope with tetrachlorosilane which can be distilled from the mixture leaving pure trimethylchlorosilane. U.S. Pat. No. 2,388,575 also reports that solvent extraction is not applicable to the separation of tetrachlorosilane and trimethylchlorosilane because of their extreme reactivity and the slight structural and solubility differences between them.

SUMMARY OF INVENTION

This invention relates to a process for effecting the separation of chlorosilanes from a first mixture of close-boiling chlorosilanes employing the principles of liquid extraction, said process comprising the steps of (1) intimately contacting said first mixture of close-boiling chlorosilanes with sulfolane and a hydrocarbon solvent, whereby a second mixture containing the close-boiling chlorosilanes, sulfolane, and hydrocarbon solvent is formed, where said hydrocarbon solvent is substantially immiscible with said sulfolane and where said hydrocarbon solvent is present in sufficient amounts in said second mixture to insure the formation of a two-phase liquid system in said second mixture, (2) allowing said second mixture to form two liquid phases where the relative amounts of the close-boiling chlorosilanes in each of said liquid phases is different from the relative amounts of the close-boiling chlorosilanes in said first mixture, and (3) separating said two liquid phases.

DETAILED DESCRIPTION OF INVENTION

The process of this invention is an example of a double solvent liquid-liquid extraction employing sulfolane and a hydrocarbon compound as co-solvents. The hydrocarbon compound or solvent should be substantially immiscible in sulfolane and should be present in sufficient amounts to insure that a two-phase liquid system is formed. In practice the process of this invention involves bringing the mixture of close-boiling chlorosilanes into intimate contact with both sulfolane and the hydrocarbon solvent. The sulfolane and the hydrocarbon solvent can be added to the chlorosilane mixture either one at a time or at the same time. The mixture containing the close-boiling chlorosilanes, sulfolane and hydrocarbon solvent is allowed to phase separate. One phase will be sulfolane-rich while the other will be hydrocarbon-rich. Due to differences in the solubility of various chlorosilanes in the two solvents, separation of the chlorosilanes will be effected. The degree of separation will depend on the selectivity of the solvents for the chlorosilane components. Finally, the sulfolane-rich or extract phase and the hydrocarbon-rich or raffinate phase are separated. The relaive amounts of the close-boiling chlorosilanes will be different in the two phases both relative to each other and to the original chlorosilane mixture.

Naturally, both the sulfolane and the hydrocarbon solvent employed in the present invention should be as dry as possible to minimize hydrolysis of the chlorosilanes. One method of removing residual water from sulfolane is to dry the sulfolane over molecular sieves. The hydrocarbon solvent can also be dried by this method. To prevent the reintroduction of water, the dried solvents, sulfolane especially, should not be exposed to water vapor.

The hydrocarbon solvent should be substantially immiscible in sulfolane and should be present in sufficient amounts to insure that a two-phase liquid system is formed where one phase is sulfolane-rich and the other phase is hydrocarbon-rich. Suitable hydrocarbon solvents include both saturated and unsaturated aliphatic hydrocarbons. The hydrocarbon solvents useful in the present invention can be linear, branched, or cyclic hydrocarbons. Examples of hydrocarbon solvents include normal alkanes such as heptane, octane, and nonane; branched alkanes such as 2,2,4-trimethylpentane, 2-methylheptane, 3-methylheptane, 4-methylheptane, 4-ethylheptane, 2,3-dimethylheptane and 2,4-dimethylheptane; alkenes such as 1-heptene, 2-heptene, 1-octene, and 2-octene; and cyclic hydrocarbons such as methylcyclohexane, cycloheptane and methylcycloheptane. In general, aromatic solvents are not useful in the present invention because of their high solubility in sulfolane. The hydrocarbon solvent should be selected such that its boiling point differs by about 10° C. or, preferably, more from that of the close-boiling chlorosilanes. This allows for the chlorosilane in raffinate phase and the hydrocarbon solvent to be separated by fractional distillation. The recovered solvent can be recycled. The preferred hydrocarbon solvents for the practice of this invention include methylcyclohexane, normal-heptane, 2,2,4-trimethylpentane, normal-octane, and normal-nonane. 2,2,4-Trimethylpentane is commerically available under the name isooctane. Blends of various hydrocarbon solvents can also be employed in the practice of this invention in the same manner.

Sulfolane is tetrahydrothiophene-1,1-dioxide and is available commercially in an anhydrous form. Pure sulfolane freezes at about 26° C. and, therefore, storage tanks and transfer lines will normally require to be heat tracing.

The process of this invention can be carried out in a batch, semi-continuous, or continuous mode. In the batch mode, the chlorosilane feed and the co-solvents can be mixed in an agitated vessel, after which the layers are settled and separated into extract and raffinate. Either the raffinate or extract can be contacted with fresh solvent (hydrocarbon solvent in the case of the extract and sulfolane in the case of the raffinate) to further effect the separation. The batch mode, using either one contact or stage or multiple contacts or stages with fresh solvent in each stage, is not very efficient. The efficiency of the liquid-liquid extraction process is improved greatly by using countercurrent flow or countercurrent extraction. Countercurrent extraction can be used in a semi-continuous or continuous mode but the largest gain in efficiency is obtained when continuous countercurrent extraction is employed. In two-solvent continuous countercurrent extraction, one solvent, for example sulfolane, is fed into the top of an extraction tower, the second solvent, for example the hydrocarbon solvent, is fed into the extraction tower at the bottom, and the close-boiling chlorosilanes are fed into the tower at some intermediate point on the tower. The two solvents flow countercurrently to each other. The types of extraction towers that can be employed in countercurrent extraction include, for example, spray towers, packed towers, perforated-plate towers, baffle towers, and agitated towers. The extract phase is drawn off the bottom and the raffinate phase is taken off the top of the extraction tower. By proper adjustment of flow rates, tower design, and sufficient number of stages in the tower, an essentially complete separation of the chlorosilanes in the mixture can be achieved. Both the extract and raffinate phases can be distilled to obtained the chlorosilane components and recover the sulfolane and hydrocarbon solvent. The recovered sulfolane and hydrocarbon solvent can be recycled to the extraction tower.

The extraction techniques discussed briefly here are well known in the art. The interested reader is referred to the following references for more details: (1) T. K. Sherwood and R. L. Pigford, *Absorption and Extraction*, McGraw-Hill, New York (1952), Chapter X; (2) L. Alders, *Liquid-Liquid Extraction*, Elsevier, New York (1955); and (3) W. L. McCabe and J. C. Smith, *Unit Operations of Chemical Engineering* (Third Edition), McGraw-Hill, New York (1976), Chapter 20.

In an preferred embodiment of the present invention, the sulfolane and hydrocarbon solvent are introduced into an extraction tower or column in a countercurrent relationship. The close-boiling chlorosilane mixture to be separated is introduced at a point on the tower or column intermediate between the points where the solvents are introduced. The procedure of the present invention can be used to separate chlorosilanes from mixtures of close-boiling chlorosilanes. If the boiling points of the non-azeotropic chlorosilanes differ by more than about 10° C. at atmospheric pressure then separation of the chlorosilanes by conventional fractional distillation is probably the method of choice. If, however, the boiling points of the chlorosilanes differ by less than 10° C. at atmospheric pressure, especially if they differ by less than 5° C., or if they form an azeotropic mixture then the procedure of this invention may be used to advantage. The chlorosilanes which may be separated by the method of this invention includes compounds of the general formula $$R_nSiCl_{4-n}$$

where n=0,1,2, or 3 and R is an alkyl or aromatic radical. The chlorosilanes include, for example, the various methylchlorosilanes, the various ethylchlorosilanes, the various propylchlorosilanes, the various butylchlorosilanes, the various phenyl chlorosilanes, as well as silicon tetrachloride. Also included are the mixed organochlorosilanes such as ethylmethyldichlorosilane, phenylmethyldichlorosilane, and ethyldimethylchlorosilane. The present invention is especially suited for the separation of (1) dimethyldichlorosilane and methyltrichlorosilane which have a boiling point difference of less than 5° C. at atmospheric pressure, (2) phenylmethyldichlorosilane and phenyltrichlorosilane which boil within 5° C. of each other at atmospheric pressure, and (3) trimethylchlorosilane and tetrachlorosilane which boil within 5° C. at atmospheric pressure and form an azeotropic mixture. Other chlorosilanes that may be present do not adversely effect the separation of the close-boiling chlorosilanes.

The temperature and pressure at which the present invention is carried out are not critical. Care should be taken, however, to prevent exposure of the sulfolane to temperatures at which it will freeze. Chlorosilanes and the hydrocarbon solvent in the sulfolane can significantly lower the freezing point of sulfolane. For economic reasons in the operation of the extraction tower, however, it is preferred that the temperature be close to ambient (but above the freezing point of the sulfolane mixture) and the pressure be close to atmospheric.

The following examples are illustrative only and shall not be construed as limiting the invention. In the examples, the solvent power or selectivity is expressed as the selectivity coefficient, $\beta$, as defined by the formula $$\beta = (Y_A/Y_B)(X_B/X_A)$$

where $Y_A$ and $Y_B$ are the weight percentages of chlorosilanes A and B, respectively, in the sulfolane phase and $X_A$ and $X_B$ are the weight percentages of chlorosilanes A and B, respectively, in the hydrocarbon phase. If there is no enrichment of one chlorosilane relative to the other by the practice of liquid-liquid extraction using sulfolane and a hydrocarbon solvent, then $\beta$ equals one. Values of $\beta$ different from one indicate enrichment of the components of the chlorosilane mixture. Values of $\beta$ significantly different from one indicate significantly more enrichment than do values close to one. The reader should be aware that the selectivity coefficient $\beta$, as determined here, is not a constant and can vary as a function of concentration of the various components. The value of $\beta$, however, can be used to predict the usefulness of a given solvent system for the separation of close-boiling chlorosilanes using the procedures of this invention. Unless otherwise specified, all experimental work was carried out at ambient temperature (about 22° C.). The sulfolane was dried over 4A molecular sieves. The hydrocarbon solvents were sufficiently dry so that additional drying was not required.

Examples 1-3 show the distribution of various chlorosilanes, each taken separately, between sulfolane and various hydrocarbon solvents. The hydrocarbon solvents were 2,2,4-trimethylpentane, normal-octane, and methylcyclohexane.

EXAMPLE 1

This example shows the partition of dimethyldichlorosilane (component A) and methyltrichlorosilane (component B), taken separately, between sulfolane and various hydrocarbon solvents. Each chlorosilane was separately mixed with a 1:1 (by weight) mixture of sulfolane and the hydrocarbon solvent. For each chlorosilane, four solutions containing about 2.5, 5.0, 20 and 33% (by weight of total mixture) of the chlorosilane in the sulfolane/hydrocarbon mixture were prepared. The mixtures were vigorously shaken and then were phase separated by centrifugation. Samples of each phase were then analyzed to determine the chlorosilane content by titrating the sample in a 1:1 toluene and n-butyl alcohol solution with a bromocresol purple indicator using a 0.01 N or 0.1 N alcoholic KOH solution.

Although, each chlorosilane was present in the sulfolane/hydrocarbon mixture separately, we have chosen to represent the results in terms of $\beta$-vlues calculated from the data obtained where the chlorosilanes were present in equal amounts. This approach assumes that the solubility of a given chlorosilane is independent of the presence of the other chlorosilane. All mixtures contained sulfolane in addition to the listed hydrocarbon solvent. It must be remembered that these $\beta$-values are estimated from data for the individual chlorosilanes in the sulfolane/hydrocarbon mixture.

| | | $\beta$-Value | | |
|---|---|---|---|---|
| $Me_2SiCl_2$ | $MeSiCl_3$ | 2,2,4-trimethyl pentane | n-octane | methyl cyclohexane |
| 2.5% | 2.5% | 1.7 | 1.7 | 1.5 |
| 5.0% | 5.0% | 1.6 | 1.8 | 1.4 |
| 20% | 20% | 1.5 | 1.7 | 1.5 |
| 33% | 33% | 1.6 | 1.6 | 1.5 |

Based on these results, one skilled in the art would know that a sulfolane/hydrocarbon mixture is a suitable solvent system for the separation of dimethyldichlorosilane and methyltrichlorsilane mixtures.

EXAMPLE 2

This example shows the partition of trimethylchlorosilane (component A) and tetrachlorosilane (component B), taken separately, between sulfolane and various hydrocarbon solvents. The procedure employed here was exactly as described in Example 1. Again it should be remembered that these $\beta$-values are estimated from data from experimental runs where each chlorosilane was singly present in a mixture of sulfolane and hydrocarbon solvent.

| | | $\beta$-Value | | |
|---|---|---|---|---|
| $Me_3SiCl$ | $SiCl_4$ | 2,2,4-trimethyl pentane | n-octane | methyl cyclohexane |
| 2.5% | 2.5% | 2.7 | 2.7 | 2.1 |
| 5.0% | 5.0% | 2.6 | 3.3 | 2.7 |
| 20% | 20% | 3.1 | 3.2 | 2.7 |
| 33% | 33% | 3.0 | 3.3 | 2.8 |

One skilled in the art would know, based on the calculated $\beta$-values, which are significantly different from 1, that a mixture of sulfolane and hydrocarbon solvent is a suitable solvent system for the liquid extraction of mixtures of trimethylchlorosilane and tetrachlorosilane.

EXAMPLE 3

This example shows the partition of phenylmethyldichlorosilane (component A) and phenyltrichlorosilane (component B), taken separately, between sulfolane and various hydrocarbon solvents. The procedure employed here was exactly as described in Example 1. Again it should be emphasized that these calculated $\beta$-values are estimated from data where each chlorosilane was present alone in the sulfolane/hydrocarbon mixture.

| | | $\beta$-Value | | |
|---|---|---|---|---|
| $PhMeSiCl_2$ | $PhSiCl_3$ | 2,2,4-trimethyl pentane | n-octane | methyl cyclohexane |
| 2.5% | 2.5% | 2.0 | 2.3 | 2.7 |
| 5.0% | 5.0% | 2.0 | 2.6 | 2.4 |
| 20% | 20% | 2.8 | 2.6 | 2.4 |
| 33% | 33% | 2.4 | 2.5 | 2.4 |

One skilled in the art would know that, based on the calculated $\beta$-values, that a mixture of sulfolane and hydrocarbon solvent is a suitable solvent system for the liquid extraction of mixture of phenylmethyldichlorosilane and phenyltrichlorosilane.

Examples 4-7 show the distribution of various chlorosilanes, in the presence of each other, between sulfolane and 2,2,4-trimethylpentane.

EXAMPLE 4

This example shows the partition of mixtures of dimethyldichlorosilane (component A) and methyltrichlorosilane (component B) between 2,2,4-trimethylpentane and sulfolane as a function of solvent ratios and temperature. Mixtures containing 2.5 g dimethyldichlorosilane, 2.5 g methyltrichlorosilane, 5.0 g sulfolane, and an amount of 2,2,4-trimethylpentane as specified in the Table below were vigorously shaken and then phase separated by centrifugation. Samples of the extract and raffinate phase were analyzed on a gas-liquid chromatograph (glc) using a ⅛ inch by 20 foot stainless steel column packed with 20% of a mixture consisting of 80% SF-1265 (a siloxane copolymer containing trifluoropropylmethylsiloxy and dimethylsiloxy units) and 20% OV-1 (a polydimethylsiloxane) on Chromsob P (80–100 mesh). The packing material was supplied by Supelco Inc., Bellefonte, Pa. The analyses were carried out with temperature programming from 50° to 220° C. at a rate of 4° C./minute.

| Temp, °C. | 2,2,4-trimethyl pentane, grams | β-Value |
|---|---|---|
| 22 | 2.5 | 1.4 |
| 22 | 2.5 | 1.3 |
| 22 | 5.0 | 1.6 |
| 22 | 5.0 | 1.4 |
| 22 | 10.0 | 1.5 |
| 22 | 10.0 | 1.6 |
| 62 | 2.5 | 1.3 |
| 62 | 2.5 | 1.3 |
| 62 | 5.0 | 1.4 |
| 62 | 5.0 | 1.4 |
| 62 | 10.0 | 1.6 |
| 62 | 10.0 | 1.4 |

Neither the solvent ratio or temperature appears to greatly effect the selectivity coefficient in this system. The amount of 2,2,4-trimethylpentane in the sulfolane phase averaged about 1.1% by weight at 22° C. and about 1.8% by weight at 62° C. The amount of sulfolane in the hydrocarbon phase was nil in all cases. One skilled in the art would known that sulfolane and a hydrocarbon solvent mixture is a suitable solvent system for the liquid extraction of mixtures of dimethyldichlorosilane and methyltrichlorosilane.

EXAMPLE 5

This example shows the partition of mixtures of dimethyldichlorosilane (component A) and methyltrichlorosilane (component B) between 2,2,4-trimethylpentane and sulfolane where the ratio of the chlorosilanes is varied. The same procedure was used here as described in Example 4 except that the mixture consisted of 5 g sulfolane and 5 g 2,2,4-trimethylpentane and varying amounts of chlorosilanes as shown in the Table below.

| Chlorosilanes in mixture, grams | | |
|---|---|---|
| $Me_2SiCl_2$ | $MeSiCl_3$ | β |
| 3.75 | 1.25 | 1.6 |
| 2.5 | 2.5 | 1.6 |
| 2.5 | 2.5 | 1.4 |
| 1.25 | 3.75 | 1.5 |

The selectivity coefficient does not appear to vary over the concentration of chlorosilanes employed. The sulfolane phase of the above mixtures contained on the average about 1.0% by weight of the hydrocarbon solvent. The amount of sulfolane found in the hydrocarbon phase was nil.

One skilled in the art would know from a consideration of these results that a sulfolane and hydrocarbon mixture can allow for the separation of dimethyldichlorosilane and methyltrichlorosilane mixture using the principles of liquid-liquid extraction.

The selectivity coefficients determined in Example 1 and this Example 5 are in reasonable agreement even though the values of Example 1 were determined by separately examining each chlorosilane in the mixed solvent system. Therefore it appears that the assumption made in Example 1, that each of these chlorosilanes has a negligible effect on the solubility of the other, was reasonable.

EXAMPLE 6

This example shows the partition of mixtures of methylphenyldichlorosilane (component A) and phenyltrichlorosilane (component B) between 2,2,4-trimethylpentane and sulfolane. The same procedure was used here as described in Example 4 except that the glc analysis was carried out with temperature programming from 50° to 250° C. at 4° C./minute. Samples were prepared containing 5.0 g of 2,2,4-trimethylpentane, 5.0 g sulfolane, and varying amounts of the two chlorosilanes as indicated in the Table below.

| Chlorosilanes in mixture, grams | | |
|---|---|---|
| $PhMeSiCl_2$ | $PhSiCl_3$ | β |
| 4.5 | 0.5 | 2.3 |
| 2.5 | 2.5 | 3.0 |
| 0.5 | 4.5 | 2.4 |

These results are in reasonable agreement with the β-values determined in Example 3 where it was assumed that the chlorosilanes would have a negligible effect on the solubility properties of each other.

One skilled in the art would know that the sulfolane and hydrocarbon solvent system is suitable for the separation of phenylmethyldichlorosilane and phenyltrichlorosilane mixtures using liquid-liquid extraction procedures.

EXAMPLE 7

The example shows the partition of mixtures of trimethylchlorosilane (component A) and tetrachlorosilane (component B) between sulfolane and 2,2,4-trimethylpentane. Mixtures containing 5.0 g sulfolane, 5.0 g 2,2,4-trimethylpentane, and varying amounts of chlorosilanes, as indicated in the Table below, were prepared and evaluated using the same procedures as in Example 4.

| Chlorosilanes in mixture, grams | | |
|---|---|---|
| $Me_3SiCl$ | $SiCl_4$ | β |
| 0.5 | 4.5 | 6.0 |
| 1.5 | 3.5 | 8.6 |
| 2.5 | 2.5 | 15.0 |
| 4.5 | 0.5 | 18.4 |

The selectivity coefficient of this system is not independent of the concentration of the chlorosilanes. The value of β increases as the ratio of trimethylchlorosilane to tetrachlorosilane increases. Additionally, the values for β found here for mixtures of the chlorosilanes do not agree with the values obtained in Example 2 where the solubility of each chlorosilane was determined in the absence of the other.

This date shows that the separation of mixtures of trimethylchlorosilane and tetrachlorosilane using the principles of liquid-liquid extraction with sulfolane and a hydrocarbon solvent should be highly favorable. This is especially true since these chlorosilanes form an azeotropic mixture which can only be separated by complicated physical or chemical techniques (as described in the Noll reference cited earlier).

From a consideration of the data here, one skilled in the art would know the liquid extraction using sulfolane and a hydrocarbon solvent is an attractive method for the separation of close-boiling chlorosilanes. Liquid extraction could be used alone or combined with the more conventional separation techniques. For example, liquid extraction could be used to concentrate a specific chlorosilane in a mixture followed by conventional or other separation techniques for the final purification of the specific chlorosilane from the concentrated mixture.

That which is claimed is:

1. A process for effecting the separation of chlorosilanes from a first mixture of close-boiling chlorosilanes employing the principles of liquid extraction, said process comprising the steps of
(1) initimately contacting said first mixture of close-boiling chlorosilanes with sulfolane and a hydrocarbon solvent, whereby a second mixture containing the close-boiling chlorosilanes, sulfolane, and hydrocarbon solvent is formed, where said hydrocarbon solvent is substantially immiscible with said sulfolane and where said hydrocarbon solvent is present in sufficient amounts in said second mixture to insure the formation of a two-phase liquid system in said second mixture,
(2) allowing said second mixture to form two liquid phases where the relative amounts of the close-boiling chlorosilanes in each of said liquid phases is different from the relative amounts of the close-boiling chlorosilanes in said first mixture, and
(3) separating said two liquid phases.

2. A process as defined in claim 1 wherein said first mixtures of close-boiling chlorosilanes contains at least two different chlorosilanes of the formula $$R_n SiCl_{4-n}$$

where n is equal to 0,1,2, or 3 and R is an alkyl or aromatic radical containing, from 1 to 6 carbon atoms.

3. A process as defined in claim 2 wherein said first mixture of close-boiling chlorosilane contains methyltrichlorosilane and dimethyldichlorosilane.

4. A process as defined in claim 2 wherein said first mixture of close-boiling chlorosilanes contains tetrachlorosilane and trimethylchlorosilane.

5. A process as defined in claim 2 wherein said first mixture of close-boiling chlorosilanes contains phenyltrichlorosilane and methylphenyldichlorosilane.

6. A process as defined in claim 1, 2, 3, 4, or 5 wherein the hydrocarbon solvent is selected from the group consisting of methylcyclohexane, normal-heptane, 2,2,4-trimethylpentane, normal-octane, and normal-nonane.

7. A process as defined in claim 1, 2, 3, 4, or 5 wherein the sulfolane and hydrocarbon solvent are separately introduced into an extraction tower or column in a countercurrent relationship.

8. A process as defined in claim 7 wherein each of said two liquid phases obtained in step (3) are individually distilled to obtain the separated close-boiling chlorosilanes and recover both the sulfolane and the hydrocarbon solvent.

* * * * *

UNITED STATES PATENT AND TRADEMARK OFFICE
CERTIFICATE OF CORRECTION

PATENT NO. : 4,402,796
DATED : September 6, 1983
INVENTOR(S) : Ollie W. Marko; Stefan F. Rentsch It is certified that error appears in the above—identified patent and that said Letters Patent is hereby corrected as shown below:

In Column 2, line 39; the line reading "phase are separated. The relaive amounts of the close-" should read "phase are separated. The relative amounts of the close-"

In Column 3, line 11; the line reading "nonane. 2,2,4-Trimethylpentane is commerically avail-" should read "nonane. 2,2,4-Trimethylpentane is commercially avail-"

In Column 5, line 37; the line reading "chosen to represent the results in terms of β-vlues calcu-" should read "chosen to represent the results in terms of β-values calcu-"

Signed and Sealed this

Twenty-first Day of February 1984

[SEAL]

Attest:

GERALD J. MOSSINGHOFF

Attesting Officer

Commissioner of Patents and Trademarks